United States Patent
Neumann et al.

(10) Patent No.: US 9,492,588 B2
(45) Date of Patent: Nov. 15, 2016

(54) ANTIBACTERIAL AND OSTEOINDUCTIVE IMPLANT COATING, METHOD OF PRODUCING SUCH COATING, AND IMPLANT COATED WITH SAME

(71) Applicant: DOT GmbH, Rostock (DE)

(72) Inventors: Hans-Georg Neumann, Rostock (DE); Cornelia Prinz, Rostock (DE)

(73) Assignee: DOT GMBH, Rostock (DE)

( * ) Notice: Subject to any disclaimer, the term of this patent is extended or adjusted under 35 U.S.C. 154(b) by 0 days.

(21) Appl. No.: 13/746,461

(22) Filed: Jan. 22, 2013

(65) Prior Publication Data
US 2013/0189323 A1    Jul. 25, 2013

(30) Foreign Application Priority Data

Jan. 23, 2012  (DE) .................. 10 2012 001 260

(51) Int. Cl.
*A61L 27/32*  (2006.01)
*A61L 27/54*  (2006.01)
*A61L 27/56*  (2006.01)

(52) U.S. Cl.
CPC ............. *A61L 27/32* (2013.01); *A61L 27/54* (2013.01); *A61L 27/56* (2013.01); *A61L 2300/102* (2013.01); *A61L 2300/404* (2013.01)

(58) Field of Classification Search
None
See application file for complete search history.

(56) References Cited

U.S. PATENT DOCUMENTS

2010/0249925 A1* 9/2010 Blunn et al. ............... 623/11.11
2010/0286790 A1  11/2010 Gruner et al.
2011/0008407 A1  1/2011 Gan et al.

FOREIGN PATENT DOCUMENTS

| WO | 9953971 A1 | 10/1999 |
|---|---|---|
| WO | 02/05862 A1 | 1/2002 |
| WO | 2009062671 A2 | 5/2009 |
| WO | 2009111307 A2 | 9/2009 |
| WO | 2010112044 A1 | 10/2010 |

OTHER PUBLICATIONS

Prinz (Antibacterial Titanium/Calcium Phosphate Implant Surfaces, Key Eng. Mater. 396 (2009) pp. 299-302).*
Heidenau (A novel antibacterial titania coating: Metal ion toxicity and in vitro surface colonization, J. Mater. Sci.: Mater. Med. 16 (2005) pp. 883-888).*

* cited by examiner

*Primary Examiner* — Bethany Barham
*Assistant Examiner* — Dominic Lazaro
(74) *Attorney, Agent, or Firm* — McNees Wallace & Nurick LLC

(57) ABSTRACT

A calcium phosphate/copper coating for an implant is provided which includes highly porous calcium phosphate and predominantly discontinuously distributed copper. The highly porous calcium phosphate first forms a highly porous calcium phosphate layer in which the copper has been incorporated so as to be discontinuously distributed, to form the calcium phosphate/copper coating. Further provided are a method of producing such a calcium phosphate/copper coating and an implant coated therewith.

18 Claims, 2 Drawing Sheets

ANTIBACTERIAL AND OSTEOINDUCTIVE IMPLANT COATING, METHOD OF PRODUCING SUCH COATING, AND IMPLANT COATED WITH SAME

The present invention relates to an antibacterial and at the same time osteoinductively active coating for implants, in particular for metallic implants and for implants that are sufficiently conductive for an electrochemical coating, a method of producing such a coating, and an implant having such a coating.

It is already known from the prior art that implant surfaces need to be modified for an optimum integration of the implants in the surrounding body tissue. This requires these surfaces to be bioactive. This means that tissues or cells are specifically influenced, that is, with a view to their differentiation and proliferation, by the implant surface such that they enter into a durable, force-fitting bond with the implant surface.

The biocompatibility of implants, which is also essentially determined by the surface features, has been decisively improved by the research activities over the last few years. In many cases these surface properties need to be designed independently of the properties of the implant material, for example by a coating (Prinz, C: Funktionalisierung von Implantatoberflächen. Dissertation, University of Rostock, 2009).

About half a million hip endoprostheses are implanted each year worldwide. An implant-induced infection is still one of the most dreaded complications in this regard (van Osten, U., Salito, A., Breme, F., Aits, M., Huihagel, K., 2008: http://www.gfe-online. de/opencms2/export/site s/default/PDF/Veroeffentlichungen/Max-schneidern_porxserx4FEE2.pdf, 15 Nov. 2008) and constitutes the principal cause of revision surgery. It is therefore of major importance to design implant surfaces such that they have not only a cell-stimulating, but also an antibacterial effect.

Since the 1980s the combination of plasma-sprayed titanium (TPS) and hydroxylapatite (HA), a poorly soluble calcium phosphate phase, has been considered the prior art for the coating of implants. Calcium phosphates are used in this connection since, as mineral components of bone tissue, they have bioactive properties, i.e. they assist in bone formation. The hydroxylapatite is applied onto the implant surfaces in a thickness of >50-200 μm, likewise using a plasma spraying method.

It has turned out to be a disadvantage here that the HA powder thermally decomposes during the spraying process, which, inter alia, results in locally different solubilities and may lead to undermining or detachment of the coating.

What is meant here is that the porosity and, hence, the layer quality are influenced by thermal influences due to the plasma spraying in such a way that the layer applied is monolithic. The low porosity leads to the poor solubility of the plasma-sprayed calcium phosphate phase. Further, complex geometries are difficult to coat by means of plasma spraying.

Amorphous calcium phosphate may, for example, lead to layer delaminations and flaking because of its very high solubility in vivo. As a consequence of such layer delaminations, formation of a connective tissue capsule may occur in the gap produced, which would eventually result in an aseptic loosening of the implant (see Heimann R.: Entwicklung biokeramischer Beschichtungen für Hüftendoprothesen Teil 2; www.tu-clausthal.de/presse/tucontact/2005/Mai/pdf).

Therefore, electrochemically deposited calcium phosphate layers have been used on bone implants for about 20 years, with the objective of improving the bond between the bone tissue and the implant. This is disclosed, for example, in U.S. Pat. Nos. 5,205,921, 5,310,464, U.S. 2008/0261034, EP 774 982 A1, U.S. Pat. No. 5,759,376, DE 195 04 386, EP 1 301 220 A1, Redepenning, J. et al.: Chem. Mater. 2 (1990) 625-7, and Kumar, M. et al.: J. Biomed. Mat. Res. 45[1999] 302-10. Calcium phosphate layers deposited on implants from electrolytic baths are very similar in their genesis to the processes occurring in bone growth. Their microporous structure can be maintained as no thermal influences appear. The microporous structure favors an immobilization of cells proceeding from which new bone tissue can form, with which the implant can grow together as in normal wound healing.

In addition, it has been known for a few years from the literature that the degree of bioactivity of a layer increases with its instability in a physiological environment. This means that from what is currently known, the bioactive coatings need to be present on the implant surfaces only until such time as the osteointegration of the implant has been attained, that is, a structural bond has been established. The local increase in the calcium ion and phosphate ion concentrations in the healing-in zone of the implant provides good conditions for the proliferation and differentiation of osteoblasts responsible for bone formation (Ducheyne, P. et al.: Biomaterials 11 (1990) 531-40). Calcium phosphates such as brushite and monetite which, in comparison with hydroxylapatite, have a very much higher solubility, are thus of a special importance specially to the healing-in phase of the implant into the bone since, owing to the higher porosity, they have a higher solubility, whereby the concentrations of the calcium ions and phosphate ions quickly increases.

As already mentioned at the outset, an implant-induced infection with bacteria constitutes the most dreaded complication. Therefore, there is a particularly great interest in configuring the implant surfaces such as to additionally provide them with an antibacterial effect.

The bacteriostatic properties of copper have already been described in the literature many times, such as, for example, in Hubacher et al. N Engl J Med 345 (2001) 561-7, and in the above-mentioned dissertation by Prinz. It has been known for some time that, in addition to its angiogenesis-promoting effect, copper has an antibacterial effect also in a free form not bound to proteins. Like with silver, one speaks of the oligodynamic effect here. Although the mechanism of action is not yet fully clear, it is considered to be certain that metal cations attack the cells at various points and in this way inactivate physiological functions such as, e.g., the synthesis of the cell membrane, of RNA and DNA, the translation or protein synthesis. The copper ions are intended to prohibit the adhesion and reproduction of clinical bacteria such as *Staphylococcus aureus* on the implant surface and prevent the reproduction thereof in the surrounding body tissue by a defined release rate.

The great advantage of the copper ions, as opposed to antibiotics, resides in that bacteria will not develop resistances when the copper concentrations decrease while the antibacterial effect is already reached at concentrations that do not yet cause cell damage (Egler, M. "Rolle von RpoE-homologen Sigmafaktoren in der Schwermetall-Homöostase von *Escherichia coli* and Cupriavidus metallidurans", Dissertation, Martin-Luther University of Halle-Wittenberg 2005). Copper ions are of essential importance to cell metabolism and are present in the body media with concentrations of approx. 1 mg/l. A local increase in this concentration to ten times as much is sufficient to achieve a considerable antibacterial effect. A anti-infectious surface modification of bone implants with copper thereby offers the chance to inhibit the development of the bacteria present in the prepared implant bearing without appreciably damaging the endogenous tissue cells or impairing them in their development (above-cited publication by Hubacher et al.).

Studies carried out in relation to the influence of copper on the cell count, compared with the studies in relation to cell viability, show that while the number of cells is reduced by the released copper, the cell viability is not decisively disturbed (Dissertation by Prinz, and Suska, F., Esposito, M., Gretzer, C., Källtorp, M., Tengvall, P., Thomsen, P. (2003): IL-1α, IL-1β and TNF-α secretion during in vivo/ex vivo cellular interactions with titanium and copper, Biomaterials, Volume 24, Issue 9, April 2003, Page 1683). This means that the chemical properties of the metal ions, their compositions, and the concentrations in the tissue as a function of time are of major importance to the toxicity and the biological response (Suska, F. (2004): "On the inflammatory response to variations in biomaterial surface chemistry"; ISBN 91-628-6302-9).

To what extent copper has an influence on HIF-1 activation and thus on new vessel formation has, to date, been studied little. However, an angiogenesis-promoting effect and a VEGF induction by copper are known (Parke, A., Bhattacherjee, P., Palmer, R. M., Lazarus, N. R., 1988: "Characterization and quantification of copper sulfate-induced vascularization of the rabbit cornea", Am J Pathol 130, 173-178; and Sen et al. (2002): "Copper-induced vascular endothelial growth factor expression and wound-healing", Am J Physiol Heart Circ Physiol 282, H1821-1827).

It is furthermore known from the literature that copper has a positive effect in wound healing processes. In this connection, Borkow found that GHK-Cu2+ has an anti-inflammatory effect and promotes tissue regeneration. GHK (glycyl-L-histidyl-L-lysine) is an amino acid having a high affinity for copper. He further observed that angiogenesis and endothelial cell proliferation are stimulated by Cu2+ ions (Borkow, G. (2004): "Copper's Role in Wound Healing", Review of Literature, Property of Cupron Inc (CUPRON Better Health Through Technology™) http://www.pedorthicnewswire.com/ . . . /Copper %20Role %20 in % 20Wound %20Healing.pdf 12.04.2008). A sufficient copper supply appears to be necessary for the function of cytokines that play a role in angiogenesis, fibrin fiber formation in inflammations, and in wound healing (above-cited publication by Sen et al., and Parke et al. (1988): "Characterization and quantification of copper sulfate-induced vascularization of the rabbit cornea", Am J Pathol 130, 173-178).

Bacteria present take up exactly so much copper until a dose toxic to them is reached. Vilchez et al. (Vilchez et al. (2007): "Dominance of sphingomonas in a copper exposed biofilm community for groundwater treatment", Microbiology 153 (Pt 2) 325-37, http://www.ncbi.nlm.nih.gov/pubmed/17259604) describe that this phenomenon can be made use of for the removal of copper from groundwater. The authors refer to this process as bioaccumulation, in which both the metal ion and the microorganisms matter. This mechanism is limited solely in that new copper ions need to be available each time. This allows the conclusion that a new infection with bacteria is prevented as long as sufficient copper from a surface can be given off to the surrounding tissue.

One example of a coating that is applied by means of a thermal spraying method is shown in WO 2009/062671. A method is indicated by means of which an implant is coated in the anchoring area with a cover layer as a coating, consisting of calcium phosphate and antibacterially active ingredients. This cover layer is applied using a thermal spray method, which produces a monolithic structure. The calcium phosphate spray powder is of a grainy quality and is mixed with metal grains. The calcium phosphate portion preferably consists of hydroxylapatite; silver and/or copper are preferred for the antibacterially active ingredients.

It has further been shown that cell and bacterial adhesion processes are highly dependent on the surface quality. Above all, the chemical composition, the hygroscopic properties and also the surface roughness play a role here that is not to be neglected. In the adhesion of bacteria there exists a relationship between their size and shape and the surface topography. Carolina Diaz et al. (Diaz et al.: "Influence of the Nano-micro Structure of the Surface on Bacterial Adhesion"; Materials Research 10, No. 1, (2007) 11-14) describe that growing on of the bacteria is favored if the topological properties of the surface correspond to the shape and size of the bacteria. They examined smooth and rough copper and gold layers and found that biofilm formation was hardly, or not at all, possible on the rough copper surfaces. The high bioactivity, accompanied by the antibacterial effectiveness, of this sponge-like composite manifests itself in the excellent wetting by the body fluid present in the wound bed of the bone and the attendant adhesion of the factors contained in this fluid and stimulating osteogenesis.

The object of the invention is to provide a coating having an improved antibacterial effectiveness, and therefore to improve the connection of an implant provided with this coating with the bone.

According to the invention, this object is achieved by the features of the described embodiments and as reflected in the independent claims and advantageous further configurations as are apparent from the dependent claims.

It is the objective of the invention to provide a coating which includes antibacterially active ingredients such as copper ions which migrate from the implant surface into the body tissue at a defined release rate and there prevent the proliferation of clinical bacteria such as *Staphylococcus aureus*. The layer deposited on the surface of the bone implant is, in addition, intended to optimally assist in the healing-in of the implant into the bone while being fully resorbed, and in this way allow the direct and complete force-fitting contact of the bone with the implant. To this end, it is of advantage if the calcium phosphate layer is highly porous since this guarantees a high solubility. The subsequent introduction of the copper ions into the highly porous calcium phosphate layer ensures that the copper ions are adsorbed at the weak points of the calcium phosphate layer. In this way, the defined release rate of the copper ions can be achieved since they are distributed discontinuously and inhomogeneously in the calcium phosphate layer previously applied.

Preferably, provision is made that this layer has a highly porous structure which allows the layer to be modified in a controlled manner both during deposition and also by a post-treatment in regard to its phase composition and solubility, and thus a controlled resorption of this layer is possible. In this way the coating can be adjusted to the requirements of the site of use of the implant. The porosity of the calcium phosphate layer is associated here with the solubility of this layer, the solubility being an important parameter for the connection of the implant with the bone tissue.

More particularly, this layer is configured to elute copper ions that promote the angiogenesis of the adjacent tissue.

Besides the calcium phosphate phases, the composite layer additionally contains copper phosphate phases and copper. Accordingly, in addition to the copper ions, the calcium ions and phosphate ions that stimulate cell growth also elute from this composite layer. The highly porous calcium phosphate phase favors the adhesion of the cells. The formation of a bacterial biofilm is made more difficult or prevented by the elution of the copper ions.

The structure, composition and thickness of the composite layer may be adapted to the respective implant and the bone surrounding the implant. The production of this composite may proceed such that the individual phases are deposited at the same time or else successively, or such that portions of one phase, e.g., the more soluble calcium phosphate phase, are transformed to a less soluble phase by a chemical reaction.

In particular, the copper concentration in the coating is selected such that a high initial elution has a sufficiently antimicrobial effect by the dissolution of elemental copper and a moderate longer-term dissolution of copper phosphates does not cause any toxic effect. The copper-containing phases ensure a bacteria-free healing-in zone over a longer period of time and therefore favor the growth and stabilization of the new bone tissue. The highly porous calcium phosphate layer ensures the high solubility and the attendant high initial elution of the copper.

Based on the highly porous structure that is adjustable by the parameters of the electrochemical deposition, the composite layer cannot, and is not to, serve as a barrier between the implant and the bone, but is intended to serve as a harmonizing factor or host in the endogenous structuring of the boundary layer between the implant and the bone. Cell and bacterial adhesion processes are highly dependent on the surface quality. Above all, the chemical composition, the hygroscopic properties and also the roughness of the surface play a role here that is not to be neglected.

In a preferred embodiment, provision is made that the layer can release copper at such a rate that a copper concentration of 90 to 160 µmol/l is obtained in a body fluid surrounding the implant. The copper content in the coating is sufficiently high to develop an antimicrobial effect. The concentration of the copper ions released in the body, however, is not so high as to effect cell damage and thus an impairment of the on-growth of the implant. As a result, this copper concentration ensures that the antimicrobial effect is able to develop while any toxic consequences for the cell tissue surrounding the implant do not yet appear.

Preferably, the layer thickness amounts to 20 µm±10 µm. This small layer thickness is sufficient for ensuring that the implant grows into the cell tissue, this being made possible on the basis of the highly porous structure of the calcium phosphate layer.

Furthermore, provision is made for an implant having a coating of the type mentioned above and which, owing to the coating applied, has the advantages mentioned above with respect to angiogenesis.

Provision is made in addition for a method of producing a coating of the type mentioned above, the method including the steps of: providing a substrate, in particular an implant; coating the substrate with calcium phosphate which is deposited electrochemically; applying copper into the calcium phosphate layer. It is ensured by this method that the copper is distributed discontinuously and inhomogeneously in the highly porous calcium phosphate layer so that a defined release rate of the copper ions that have the antimicrobial effect is ensured. Also, the electrochemical deposition method allows more complex geometries of the substrate to be coated.

In a particularly preferred embodiment, provision is made that the calcium phosphate is deposited, in particular electrochemically, while the substrate is in an ultrasonic bath. The ultrasound serves to remove any calcium phosphate crystals that are bound too weakly to the implant surface. The holes produced in the layer in this process are newly coated promptly.

In particular, provision is made that the copper is electrodeposited. This offers the advantage that the copper can accumulate even in complex geometries of the substrate coated with the calcium phosphate layer.

In a particularly preferred embodiment, provision is made that the copper is deposited while the substrate is in an ultrasonic bath. The gaps in the calcium phosphate layer that are generated by the ultrasound are predominantly filled with copper here. The copper thus attaches to the weak points of the calcium phosphate layer which become apparent due to the ultrasonic bath. In addition, any poorly adhering copper ions are detached by the ultrasonic bath; these places may be provided with copper once again.

Preferably, the calcium phosphate is deposited to have a thickness of about 20 µm. Owing to the highly porous calcium phosphate layer, this thickness is already sufficient to ensure the ingrowth.

In particular, the copper is deposited with a mass of about 1 µg/mm$^2$. This deposition rate ensures that the copper concentration in the coating is selected to provide a sufficiently antimicrobial effect while, however, producing no toxic effect leading to damage to the surrounding tissue.

The invention will be explained below on the basis of illustrations and an exemplary embodiment:

FIG. 1 shows a scanning electron microscopic image of a calcium phosphate/copper coating according to the invention that was electrochemically deposited; brushite was used here for the highly porous calcium phosphate layer into which copper was incorporated discontinuously.

Figure 1:
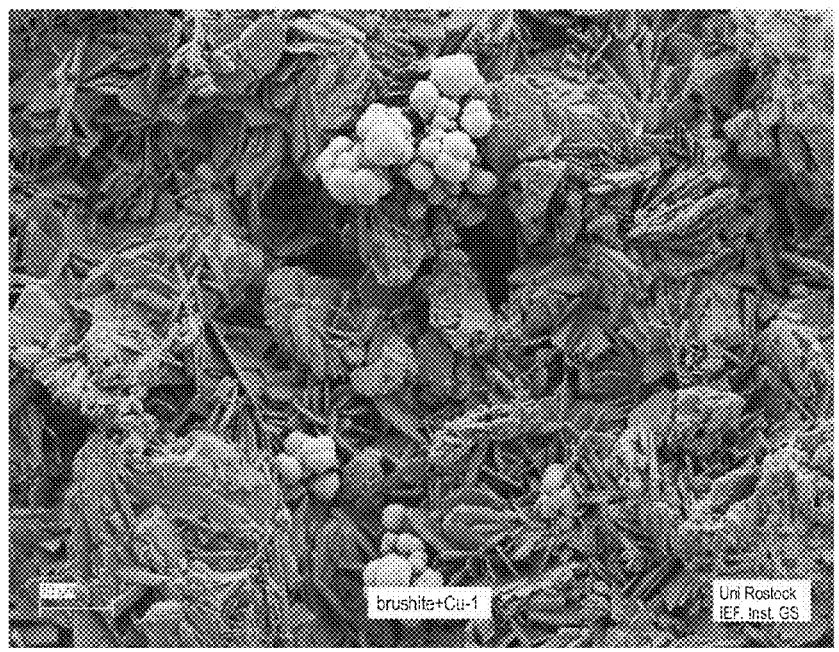
FIG. 1 shows a scanning electron microscopic image of an electrochemically deposited calcium phosphate (brushite)/copper coating according to the invention.

The highly porous structure of the calcium phosphate layer is hard to see in FIG. 1 since owing to the scanning electron microscopic image, a very detailed image was taken of the coating. However, the calcium phosphate crystallites can be recognized, which are fixed in the form of platelets or needles almost vertically on the implant surface. A large reactive surface is provided by this microporous or highly porous calcium phosphate layer for the interaction with the biological environment. Furthermore, copper ions can be recognized, which have been incorporated or embedded in the highly porous calcium phosphate layer in a discontinuously and inhomogeneously distributed fashion.

Preferably, the calcium phosphate layer has been applied onto the implant by means of an electrochemical deposition method, with the copper also having been galvanically incorporated into the existing calcium phosphate layer. By selectively varying the coating parameters, different calcium/phosphate ratios and porosities can be adjusted in accordance with requirements. In detail, the coating results from an electrochemical process in which at first, by applying a negative voltage to the metallic implant, a calcium phosphate (brushite) layer having a thickness of about 15 µm, a high porosity and therefore a high bioactivity is deposited from the electrolyte onto the highly alkaline surface of the implant. Subsequently, the copper is galvanically incorporated in the highly porous calcium phosphate layer in a discontinuous and inhomogeneous fashion, preferably from a saturated copper acetate solution.

The calcium phosphate layer and also the copper are preferably incorporated electrochemically, the coating process occurring during an ultrasonic bath. The ultrasonic bath makes sure that any weak points of the coating are detached and such points can therefore be newly coated. This applies both to the basic coating of the implant with the calcium phosphate layer and to the later introduction of the copper into the existing highly porous calcium phosphate layer. In the process of incorporating the copper it is thus further ensured that the copper is incorporated in weak points of the calcium phosphate layer. This implies that the copper is distributed discontinuously and inhomogeneously in the calcium phosphate layer.

Figure 2:
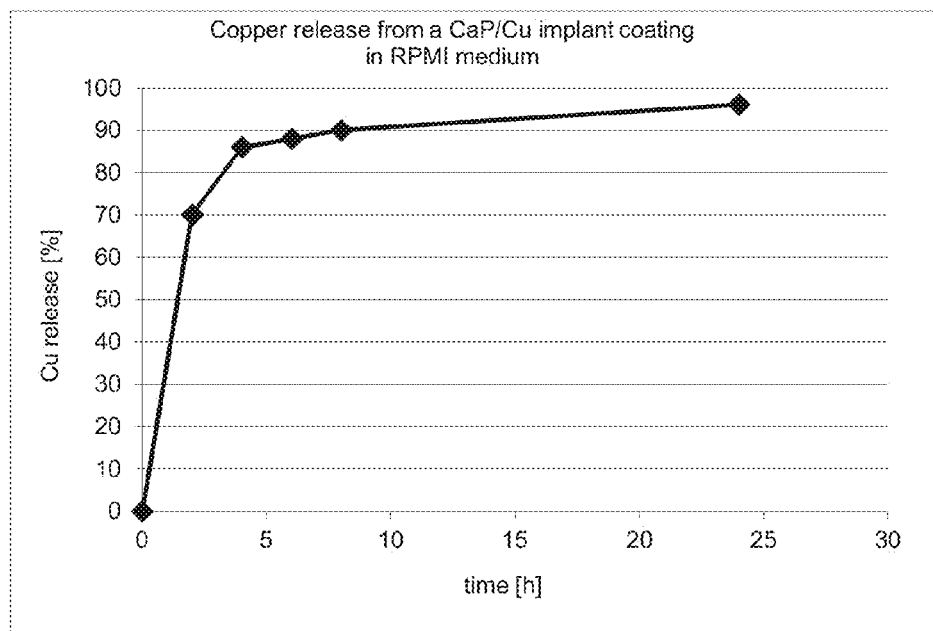
FIG. 2 shows the copper release from a calcium phosphate/copper (CaP/Cu) implant coating according to the invention in RPMI cell culture medium.

FIG. 2 shows the release of the copper from a calcium phosphate/copper coating according to the invention versus time. The discontinuously distributed copper in an RPMI cell culture medium is dissolved very rapidly. As early as after 8 hours, 90% of the copper deposited on the specimen surface can be detected in the RPMI medium. Part of the copper ions going into solution, together with the phosphate ions eluted from the calcium phosphate coating, form copper phosphates which are more difficult to dissolve and substantially account for the smaller amount of copper introduced in the following time. As already mentioned, the presence of copper stimulates angiogenesis and has a positive influence on the wound healing process. Therefore, it is of advantage that the copper is deposited rapidly in order to develop its effect accordingly.

Figure 3:
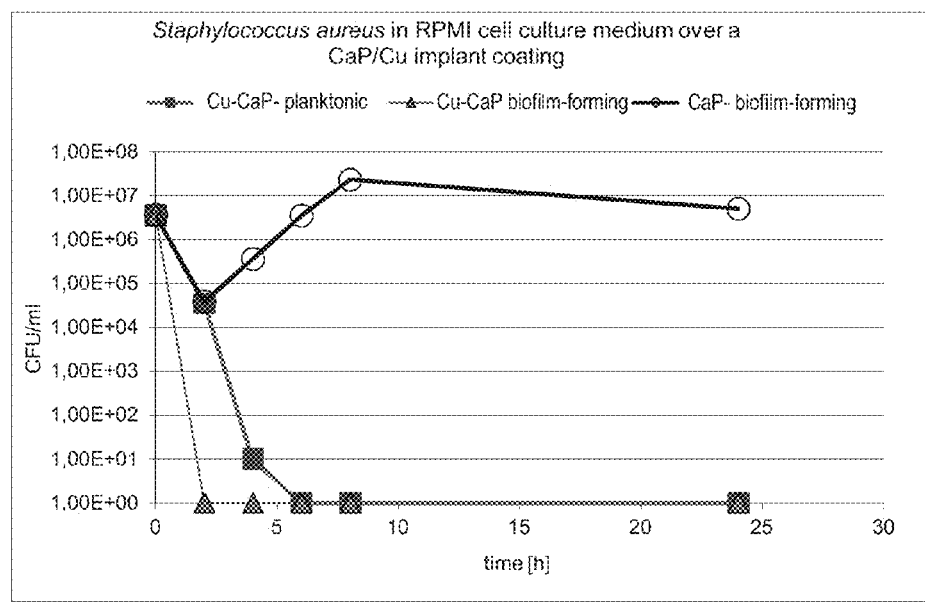
FIG. 3 shows the behavior of biofilm-forming and planktonic *Staphylococcus aureus* in RPMI cell culture medium over a CaP/Cu implant coating according to the invention and over a copper-free CaP coating.

FIG. 3 compares the behavior of biofilm-forming and planktonic *Staphylococcus aureus* in an RPMI cell culture medium of a calcium phosphate/copper coating according to the invention to a copper-free calcium phosphate coating. FIG. 3 thus illustrates more clearly the antibacterial effect of the copper introduced in the calcium phosphate layer as compared to a calcium phosphate layer without an incorporation of copper. The graph shown in FIG. 3 illustrates the bacteria concentration versus time; for examining the antibacterial effect, the clinically relevant *Staphylococcus aureus* ATCC25923 bacterial strain was used. To this end, Ti samples (thickness=1 mm, diameter=20 mm) were coated with calcium phosphate and copper (1 µg/mm$^2$) and aged for different lengths of time in 4 ml of the RPMI cell culture medium inoculated with 150 µl bacterial suspension at a temperature of 37° C. Then the bacterial concentration on the sample bodies and in the solution was determined by plating on nutrient agar and ageing at 30° C. A sample surface only coated with calcium phosphate was used as a reference. Live bacteria are clearly detectable on the latter, whereas this is not the case on the surface additionally coated with copper (CaP/Cu). This is also affirmed by laser light fluorescence microscopic images taken. In the case of the planktonic bacteria, no bacteria capable of reproduction were detectable after 6 hours.

The antibacterial effect of the copper is therefore clear. The rapid decrease in the bacterial concentration is accompanied by the very rapid copper release as has been shown in FIG. 2, the copper being able to dissolve from the highly porous calcium phosphate layer since the copper is distributed discontinuously and inhomogeneously in this highly porous layer. A further reason for the rapid release rate of the copper resides in that the copper has been incorporated predominantly in weak points of the calcium phosphate layer.

The copper-loaded CaP layer according to the invention was examined with respect to its influence on signal transduction in new vessel formation and in inflammation. It could be found that there are no indications of an appearance of cell death. CD31 protein staining even suggested an activation of the cells by copper.

The antibacterial effect of copper and the cause of the rapid copper release, which is founded in the configuration of the calcium phosphate/copper coating according to the invention, has been shown in FIGS. 1 to 3. A preferred embodiment of a substrate and the process of coating it with the calcium phosphate/copper coating according to the invention will now be indicated below.

A suitable experimental arrangement for coating a substrate in a manner according to the invention is as follows: A beaker with 100 ml of an aqueous electrolyte containing 0.1 mol/l $NH_4H_2PO_4$ and 0.167 mol/l $CaCl_2$ is placed in an ultrasonic bath. A titanium sample (1 mm thick, 20 mm in diameter) as the cathode is connected in the electrolyte to an inert carbon anode via a DC power supply unit. A highly porous, adhesively strong calcium phosphate layer (approx. 20 µg/mm$^2$) is deposited to a thickness of 20 µm at a moderate ultrasound at 6 volts in 10 minutes.

As mentioned above, when applying the copper it is also of advantage to subject the substrate to an ultrasonic bath. A suitable experimental setup here is as follows: The sample coated with calcium phosphate as the cathode is connected via a DC power supply unit to a copper anode in a saturated aqueous copper acetate solution and coated with copper at 6 volts for 10 seconds. In the process, approx. 1 µg copper/mm$^2$ is deposited.

A calcium phosphate/copper coating according to the invention has thus been applied on a substrate which has an improved antibacterial effectiveness as provided by the coating.

An implant coated in this way can now be implanted into a human body; after the implantation, the following steps may be characterized by three stages in a simplified manner:

In stage I at first the copper ions are flushed out. In the presence of bacteria, this process is accelerated by a high affinity of the bacteria for metal cations. Here, bacteria take up copper exactly until such time as their lethal dose is reached. The time period required therefor is determined by the supply of copper. This has been shown in FIGS. 2 and 3 and suitably discussed. The process described in the literature as the "race for the surface" ("race" between the endogenous cells and the microorganisms introduced during surgery), which takes place immediately after introduction of the implant, is, owing to the copper, shifted for the benefit of the cells.

In stage II, the largest local increase in the calcium ion and phosphate ion concentrations present in the boundary layer between the implant and the bone is essentially determined by the more readily soluble phases. In this stage it must be ensured that no fibrous encapsulation of the implant occurs, and its direct osteointegration is made possible in this way. The porosity of the composite first increases by the decrease in the more readily soluble phases, making room for new bone tissue.

In stage III, the less readily soluble composite portion is dissolved. The copper phosphates precipitated by the presence of copper ions determine the local ion balance and in particular assist in mineralization and angiogenesis of the new bone tissue. Once the less soluble calcium phosphate phases have been dissolved, the entire composite has been transformed into bone tissue.

After the complete dissolution of the coating described in stage III the entire composite has now been replaced by new bone and the implant has healed into the bone with a force fit.

Proceeding from first contacts of the immobilized cells with the implant through the pores of the composite, a force-fitting connection between the bone and the implant has developed from the outset by the progressive dissolution of the individual phases.

As a result, a coating for an implant is provided having an improved antimicrobial effect and at the same time speeding up the healing-in process.

The invention claimed is:

1. A calcium phosphate and copper coating for an implant comprising a highly porous calcium phosphate and predominantly discontinuously distributed copper, the highly porous calcium phosphate forming a highly porous calcium phosphate layer in which the highly porous calcium phosphate is brushite and the copper has been incorporated so as to be discontinuously distributed, to form the calcium phosphate and copper coating, the highly porous calcium phosphate layer having a higher porosity than hydroxylapatite, wherein the calcium phosphate coating comprises calcium phosphate phases as well as copper phosphate phases and electrodeposited elemental copper.

2. The calcium phosphate and copper coating according to claim 1, wherein the calcium phosphate layer has a highly porous structure which allows the calcium phosphate layer to be controllably modified during deposition and by post-treatment with respect to its phase composition and solubility.

3. The calcium phosphate and copper coating according to claim 1, wherein the calcium phosphate layer is configured to elute copper ions that promote the angiogenesis of the adjacent tissue.

4. The calcium phosphate and copper coating according to claim 1, wherein the copper concentration in the coating is selected such that a high initial elution by the dissolution of elemental copper has a sufficiently antimicrobial effect and a moderate longer-term dissolution of copper phosphates does not cause any toxic effect.

5. The calcium phosphate and copper coating according to claim 1, wherein the calcium phosphate layer can release copper at such a rate that a copper concentration of 90 to 160 µmol/l is obtained in a body fluid surrounding the implant.

6. The calcium phosphate and copper coating according to claim 1, wherein the calcium phosphate layer thickness is 20±10 µm.

7. An implant comprising a coating according to claim 1.

8. A method of producing a coating according to claim 1, comprising the steps of:
   providing a substrate;
   coating the substrate with calcium phosphate which is deposited electrochemically;
   applying copper into the calcium phosphate layer.

9. The method according to claim 8, wherein the calcium phosphate is deposited electrochemically while the substrate is in an ultrasonic bath.

10. The method according to claim 8, wherein the copper is electrodeposited.

11. The method according to claim 10, wherein the copper is deposited while the substrate is in an ultrasonic bath.

12. The method according to claim 9, wherein the calcium phosphate is deposited to a thickness of about 20 µm.

13. The method according to claim 8, wherein the copper is deposited to have a mass of about 1 µg/mm$^2$.

14. The method of claim 8, wherein the substrate is an implant.

15. The calcium phosphate and copper coating according to claim 1, wherein the copper concentration in the coating is selected such that a high initial elution by the dissolution of elemental copper has a sufficiently antimicrobial effect and a moderate longer-term dissolution of copper phosphates does not cause any toxic effect, the calcium phosphate layer releasing copper at such a rate that a copper concentration of 90 to 160 µmol/l is obtained in a body fluid surrounding the implant, and wherein the calcium phosphate layer thickness is 20±10 µm.

16. The method according to claim 8, wherein the calcium phosphate is deposited electrochemically to a thickness of about 20 µm while the substrate is in an ultrasonic bath and where the copper is deposited in an ultrasonic bath after the calcium phosphate has been deposited, the copper deposited to have a mass of about 1 µg/mm$^2$.

17. The calcium phosphate and copper coating according to claim 1, wherein the elemental copper is provided for a high initial elution and the copper phosphate phases for a moderate longer-term dissolution.

18. A calcium phosphate and copper coating for an implant comprising a highly porous calcium phosphate and predominantly discontinuously distributed copper, the highly porous calcium phosphate forming a highly porous calcium phosphate layer in which the highly porous calcium phosphate is brushite and the copper has been incorporated so as to be discontinuously distributed, to form the calcium phosphate and copper coating, the highly porous calcium phosphate layer having a higher porosity than hydroxylapatite, wherein the calcium phosphate coating comprises calcium phosphate phases as well as copper phosphate phases and copper, and wherein 90% of the deposited copper is released into a RPMI cell culture medium.

* * * * *